US011357461B2

(12) United States Patent
Garlow et al.

(10) Patent No.: US 11,357,461 B2
(45) Date of Patent: Jun. 14, 2022

(54) G-SHAPED ARM IMAGING DEVICES, SYSTEMS, AND METHODS

(71) Applicant: Medtronic Navigation, Inc., Louisville, CO (US)

(72) Inventors: David A. Garlow, Lynnfield, MA (US); Elizabeth A. Levasseur, New Boston, NH (US); John T. Hickey, Merrimack, NH (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 16/945,094

(22) Filed: Jul. 31, 2020

(65) Prior Publication Data

US 2022/0031268 A1    Feb. 3, 2022

(51) Int. Cl.
*A61B 6/00*    (2006.01)
*A61B 6/04*    (2006.01)

(52) U.S. Cl.
CPC .......... *A61B 6/4435* (2013.01); *A61B 6/0407* (2013.01); *A61B 6/4405* (2013.01); *A61B 6/54* (2013.01)

(58) Field of Classification Search
CPC ..... A61B 6/035; A61B 6/4452; A61B 6/4085; A61B 6/0407; A61B 5/061; A61B 6/483; A61B 6/405; A61B 6/4021; A61B 6/44441; A61B 6/4283; A61B 6/4405; A61B 6/032; A61B 6/06; A61B 6/066; A61B 6/4447; A61B 6/466; A61B 6/467; A61G 13/04; A61G 2200/322; F16C 17/10; A61N 5/1082; A61N 5/1067; A61N 2005/1082; A61N 2005/1085; A61N 2005/1095; A61N 2005/1091
See application file for complete search history.

(56) References Cited

U.S. PATENT DOCUMENTS 6,428,206 B1    8/2002    Watanabe
6,461,039 B1    10/2002   Klotz et al.
7,170,972 B2    1/2007    Altman
(Continued)

FOREIGN PATENT DOCUMENTS

DE    102015202082    12/2015
EP    1439784    2/2006

OTHER PUBLICATIONS

"Alphenix Biplane—Multi-Access Biplane System," Canon Medical US, Jan. 8, 2019, 14 pages [retrieved online from: www.youtube.com/watch?v=GWQmyhBFUBI].

*Primary Examiner* — Don K Wong
(74) *Attorney, Agent, or Firm* — Sheridan Ross P.C.

(57) ABSTRACT

An imaging device for obtaining 360-degree images of an anatomical feature of a patient or of another object includes an open ring having a first end, a second end, and an axis, the open ring defining an outer arc and an inner arc; a support arm configured to support the open ring and to rotate the open ring about the axis; a track extending along the open ring; a source movably disposed on the track and operable to generate signals useful for imaging; and a detector movably disposed on the track, the detector operable to detect signals generated by the source. Movement of the source and detector along the track, coupled with rotation of the open ring about the axis, enables the source and detector to travel at least 360 degrees about the axis.

20 Claims, 6 Drawing Sheets

(56) References Cited

U.S. PATENT DOCUMENTS

| | | |
|---|---|---|
| 7,434,996 B2 | 10/2008 | Wang et al. |
| 9,554,761 B2 | 1/2017 | Baumann et al. |
| 9,855,015 B2 | 1/2018 | Risher-Kelley et al. |
| 9,855,016 B2 | 1/2018 | Lee |
| 9,962,133 B2 | 5/2018 | Risher-Kelley et al. |
| 10,159,453 B2 | 12/2018 | Risher-Kelley et al. |
| 10,448,910 B2 * | 10/2019 | Johnson ............... A61B 6/4441 |
| 10,517,553 B2 | 12/2019 | Barker et al. |
| 10,573,023 B2 | 2/2020 | Crawford et al. |
| 10,928,713 B2 | 2/2021 | Okuda et al. |
| 2003/0072416 A1 * | 4/2003 | Rasche ............... A61B 6/4441 378/197 |
| 2019/0038365 A1 | 2/2019 | Soper et al. |
| 2019/0099140 A1 | 4/2019 | Garlow et al. |
| 2019/0099141 A1 | 4/2019 | Garlow et al. |

\* cited by examiner

G-SHAPED ARM IMAGING DEVICES, SYSTEMS, AND METHODS

FIELD

The present technology is related generally to imaging devices and, more particularly, to medical imaging devices capable of capturing a 360° image of an object.

BACKGROUND

The ability of a medical imaging device to spin a full 360° is key to obtaining crisp three-dimensional images of a patient. If less than 360° of travel is utilized, 3D reconstruction of the resulting image may be impossible or aspects of the 3D image may have poor quality, because the data for the omitted portion of the full 360° spin is not available.

O-arms using breakable gantries or doors are often utilized to obtain an image around a full 360° of an object. The door of such O-arms can be opened to allow the O-arm to be positioned around a patient (and, for example, a table or bed on which the patient rests, typically in a prone position). The door can then be closed so that the O-arm encircles the patient entirely, and one or more imaging sensors can "spin" around the O-arm to achieve a full 360° image of the patient or a portion thereof.

C-arms provide a lower-cost, albeit somewhat less capable, imaging option. A C-arm is an imaging device with an X-ray emission device fixed at one end of a C-shaped arm and an X-ray detector device fixed at an opposite end of the C-shaped arm, 180° of angular distance apart from the X-ray emission device. As a result, C-arms are useful for obtaining 2D images, but are incapable of a full 360° spin and therefore cannot obtain a full 360° image.

SUMMARY

A G-shaped arm according to embodiments of the present disclosure achieves a 360° spin without the use of door, thus obtaining the benefits of both a C-arm (such as lower cost and easier maneuverability) and an O-arm (including in particular the ability to complete a 360° spin and thus obtain a full 360° image). A G-shaped arm according to embodiments of the present disclosure comprises an arcuate arm that can rotate approximately 180° to 270°. Additionally, the imaging system or a portion thereof travels around the G-shaped arm to make up the difference in travel necessary to achieve a full 360° of rotation of the imaging system. Thus, for example, if the arcuate arm rotates 180°, then the imaging sensor may also travel an angular distance of 180° along or proximate to the arcuate arm, and if the arcuate arm rotates 270°, then the imaging sensor may travel an angular distance of 90° or more along or proximate to the arcuate arm.

An imaging device according to at least one embodiment of the present disclosure comprises: an open ring having a first end, a second end, and an axis, the open ring defining an outer arc and an inner arc; a support arm configured to support the open ring and to rotate the open ring about the axis; a track extending along the open ring; a source movably disposed on the track and operable to generate signals useful for imaging; and a detector movably disposed on the track, the detector operable to detect signals generated by the source. Movement of the source and detector along the track, coupled with rotation of the open ring about the axis, enables the source and detector to travel at least 360 degrees about the axis.

The track may not extend beyond the first end or the second end. The source and the detector may be positioned 180 degrees apart around the track. The imaging device may further comprise a trolley movably disposed on the track, the trolley extending between a third end proximate the first end and a fourth end proximate the second end. The source and the detector may be fixedly secured to the trolley between the third end and the fourth end. The third end may never pass the first end, and the fourth end may never pass the second end. Movement of the source and the detector along the track may be selectively independent of rotation of the open ring relative to the support arm. Each of the source and the detector may be movable along the track toward the first end and away from the first end. The outer arc may have an arc measure between 270 degrees and 350 degrees. The imaging device may further comprise a base to which the support arm is secured, the base selectively movable on a plurality of omnidirectional wheels. The track may extend along or proximate the inner arc. Each of the source and the detector may be configured to move along the track through an arc of 90 degrees or less.

A G-shaped arm system according to at least another embodiment of the present disclosure comprises: an arcuate arm defining an axis and extending from a first end to a second end through an arc of at least 270 degrees but not more than 345 degrees; a support structure configured to rotate the arcuate arm about the axis; and an imaging system movably secured to the arcuate arm. The imaging system comprises a source and a detector. Movement of the arcuate arm about the axis together with movement of the imaging system relative to the arcuate arm provides at least 360 degrees of coverage about the axis.

The source and the detector may be independently movable relative to the arcuate arm. The source and the detector may remain 180 degrees apart on the arcuate arm. No component of the imaging system may extend past the first end or the second end. The support structure may be selectively movable on a plurality of omnidirectional wheels.

A method of obtaining a 360-degree image according to at least yet another embodiment of the present disclosure comprises: aligning an axis of an arcuate arm with an object to be imaged, the arcuate arm defining an arc having an arc measure between 180 and 350 degrees, the arcuate arm rotatably supported by a tower configured to selectively rotate the arcuate arm about the axis; activating an imaging system movably secured to the arcuate arm, the imaging system comprising a source and a detector disposed at radial positions 180 degrees apart from each other relative to the axis; rotating the arcuate arm X degrees about the axis, where X is equal to or less than the arc measure; and moving the imaging system along the arcuate arm Y degrees about the axis, where Y is equal to or more than 360 minus X. The result of the rotating and moving steps is that the imaging system rotates through at least 360 degrees around the axis.

Moving the imaging system may further comprise moving a trolley along the arcuate arm. The source and detector may be fixedly attached to the trolley. Aligning an axis of an arcuate arm with an object to be imaged may comprise moving the tower on a plurality of omnidirectional wheels. Rotating the arcuate arm may comprise applying a torque to an outer surface of the arcuate arm. Moving the imaging system along the arcuate arm may comprise causing the imaging system to move along a track positioned along an inner surface of the arcuate arm.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1A:
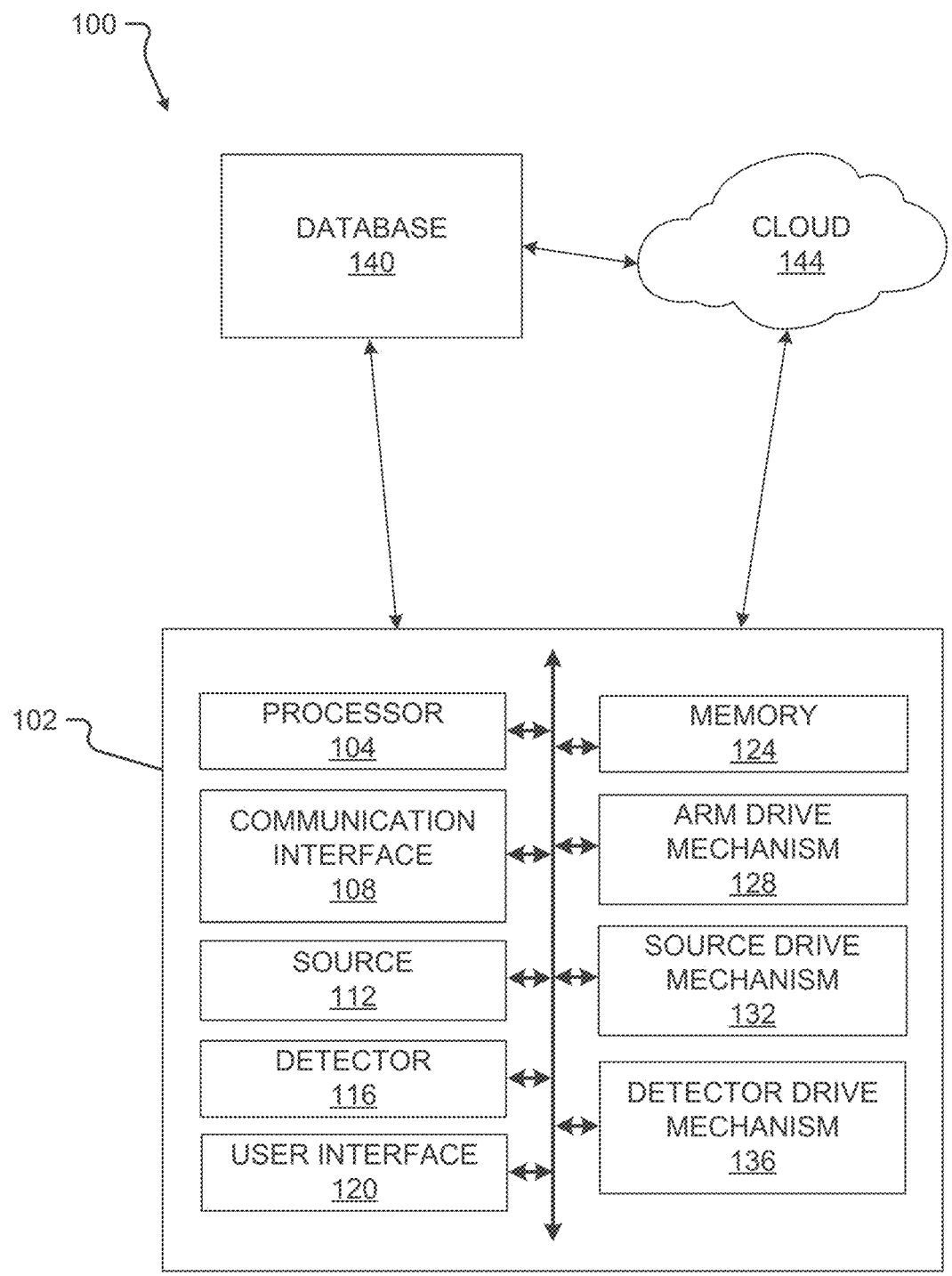
FIG. 1A is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the methods of this disclosure may be performed by a combination of units or modules associated with, for example, a computing device and/or a medical device (including a medical imaging device).

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Turning first to FIG. 1A, a block diagram of a system 100 according to at least one embodiment of the present disclosure is shown. The system 100 may be used to capture a 360° image of a patient (including of an anatomical feature of the patient) or an object. In some embodiments, the system 100 may also be used to process, store, and/or display image data associated with the captured image.

The system 100 comprises an imaging device 102, a database 140, and a cloud 144. The imaging device 102 comprises a processor 104, a communication interface 108, a source 112, a detector 116, a user interface 120, a memory 124, an arm drive mechanism 128, a source drive mechanism 132, and a detector drive mechanism 136. Each of these components is described in greater detail below. Systems such as the system 100 according to other embodiments of the present disclosure may comprise more or fewer components than the system 100.

The processor 104 of the imaging device 102 may be any processor described herein or any similar processor. The processor may be configured to execute instructions stored in the memory 124, which instructions may cause the processor to carry out one or more computing steps utilized or based on data received from or via the communication interface 108, the detector 116, the user interface 120, the database 140, and/or the cloud 144. The one or more computing steps may be steps that control the imaging device 102 to operate in any manner described herein or in any similar manner.

The communication interface 108 may be used for receiving image data from the detector 116, for receiving information (including data, instructions, and/or commands) from or via an external source (such as the database 140, and/or the cloud 144), and/or for transmitting images or other information to or via an external source (e.g., the database 140, the cloud 144). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the communication interface 108 may be useful for enabling the imaging device 102 to communicate with one or more external processors 104 (either directly or via the cloud 144), whether to reduce the time needed to accomplish a computing-intensive task or for any other reason.

The source 112 may be a source of X-ray or other radiation, and may be configured to emit radiation in a predetermined direction. The radiation may be emitted from the source 112 along a straight line or path or in a fan pattern. The source 112 may be or comprise, for example, an X-ray tube, an X-ray laser, an X-ray generator, a synchrotron, or a cyclotron. The source 112 may be useful for computed tomography (CT) imaging or other forms of X-ray imaging. In some embodiments, the source 112 generates low-coherence light useful for optical coherence tomography imaging. In such embodiments, the source 112 may be or comprise for example, one or more superluminescent diodes, ultrashort pulsed lasers, and/or supercontinuum lasers.

The detector 116 may be any device useful for detecting radiation emitted by the source 112. For example, if the source 112 generates X-ray radiation, then the detector 116 is a device for detecting X-ray radiation. If the source 112 generates low-coherence light, then the detector 116 is a detector for detecting low-coherence light. The size and shape of the detector 116 may be selected to correspond to the path or pattern of radiation emitted by the source 112. For example, if the source 112 emits radiation along a relatively straight, narrow path, then the detector 116 may be configured to detect radiation received along such a path. On the other hand, if the source 112 emits radiation in a fan pattern, then the detector 116 may have a larger size than the source 112 (which size may be based, for example, on how far away from the source 112 the detector 116 will be positioned) and may be correspondingly shaped. In some embodiments, the detector 116 may be configured to be positioned directly opposite the source 112, while in other embodiments, the detector 116 may be configured to be positioned adjacent the source 112, or in some other relation to the source 112 other than adjacent to or directly opposite the source 112. In some embodiments, the source 112 and the detector 116 are provided in a single device and/or housing (e.g., when the detector 116 is configured to detect radiation bouncing or reflecting off of an object).

In some embodiments, the source 112 and the detector 116 may be replaced by an imaging device or system that does not use one or both of a source 112 or detector 116. For example, in some embodiments of the present disclosure, a camera or other optical sensor may be used instead of the source 112 and the detector 116.

The user interface 120 may be or comprise a keyboard, mouse, trackball, monitor, television, touchscreen, and/or any other device for receiving information from a user and/or for providing information to a user of the imaging device 102. The user interface 120 may be used, for example, to receive a user selection or other user input in connection with aligning an axis of the imaging device 102 with an object to be imaged; to receive a user selection or other user input that causes or otherwise relates to activation of the imaging device 102 to obtain an image; to receive a user selection or other user input regarding one or more configurable settings of the imaging device 102; to receive a user selection or other user input regarding how and/or where to store and/or transfer image data recorded or otherwise obtained by the imaging device 102; and/or to display an image to a user based on image data recorded or otherwise obtained by the imaging device 102.

In some embodiments, the imaging device 102 comprises a plurality of user interfaces 120, which may be identical to each other or different from each other. Although the user interface 120 is shown as part of the imaging device 102, in some embodiments, the imaging device 102 may utilize a user interface 120 that is housed separately from one or more remaining components of the imaging device 102. In some embodiments, the user interface 120 may be located proximate one or more other components of the imaging device 102, while in other embodiments, the user interface 120 may be located remotely from one or more other components of the imaging device 102.

The memory 124 may be or comprise RAM, DRAM, SDRAM, other solid-state memory, any memory described herein, or any other non-transitory memory for storing computer-readable data and/or instructions. The contents of the memory 124 may, in some embodiments, be organized into one or more applications, modules, packages, layers, or engines. The memory 124 may store instructions, information, and/or data useful for completing, for example, any step of the method 400 described herein. The memory 124 may store raw data received from the detector 116, processed data generated based on or using the raw data, and any other image data. "Image data," as used herein, refers to any data corresponding to an electronically recorded or generated image—including, for example, data useful for displaying the electronically recorded or generated image on a display device, data regarding one or more parameters of the electronically recorded or generated image, and raw data from which an electronically recorded or generated image is constructed or reconstructed.

The imaging device 102 further comprises an arm drive mechanism 128, which in at least some embodiments comprises one or more motors or other torque-producing devices or systems for rotating an arcuate arm of the imaging device about an axis thereof. In some embodiments, the arm drive mechanism 128 may be configured to both support the arcuate arm of the imaging device and to cause the arcuate arm of the imaging device to rotate. In other embodiments, the arcuate arm may be movably mounted in, on, or to a support structure that also supports the arm drive mechanism 128.

In some embodiments, the arm drive mechanism 128 may comprise one or more electric motors driving one or more gears that are in force-transmitting communication with the arcuate arm. In other embodiments, the arm drive mechanism 128 may comprise one or more electric motors driving a belt and wheel/pulley system in force-transmitting communication with the arcuate arm. In still other embodiments, the arcuate arm may be part of the arm drive mechanism 128. For example, the arm drive mechanism 128 may comprise a rotor and a stator, and the rotor may be the arcuate arm.

The arm drive mechanism 128 may, in some embodiments, engage an outer surface or arc of an arcuate arm, whether with one or more wheels, one or more gears, or otherwise. For example, the arm drive mechanism 128 may comprise a motor turning a wheel, which wheel may be pressed against an outer arc or circumferential surface of the arcuate arm, such that rotation of the wheel causes the arcuate arm to rotate. In other embodiments, the arcuate arm may be provided with a plurality of gear teeth along an outer arc or circumferential surface thereof, and the arm drive mechanism 128 may comprise a motor turning a gear that engages with the plurality of gear teeth to cause the arcuate arm to rotate.

In other embodiments, the arm drive mechanism 128 may engage one or both axial side surfaces or ends of the arcuate arm. In such embodiments, the arm drive mechanism 128 may be or comprise any of the same systems, devices, and components described above, or similar systems, device, and/or components.

Operation of the arm drive mechanism 128 may be controlled by the processor 104 and/or by a controller separate from the processor 104. The arm drive mechanism 128 may be selectively activated to move the arcuate arm into a desired position prior to or following imaging of a patient or object, and/or may be selectively activated to cause the arcuate arm to rotate during imaging of a patient or object. Any motor or other torque-producing device or system, whether electric or otherwise, may be used for the arm drive mechanism 128.

The source drive mechanism 132 is configured to cause the source 112 to move along an inner arc or circumferential surface of an arcuate arm of the imaging device 102 (and thus to move around an axis of the arcuate arm while remaining equidistant from that axis). The source drive mechanism 132 may be configured to engage a track that is built into, extends from, is secured to, or is otherwise arranged along or proximate an inner arc or circumferential surface of the arcuate arm. In some embodiments, the source drive mechanism 132 may be configured to engage a track that is built into, extends from, is secured to, or is otherwise arranged along or proximate one or both axial side surfaces or ends of the arcuate arm. Any such track may extend along an entirety of the arcuate arm or along a portion of the arcuate arm. In some embodiments, the track may extend beyond one or both ends of the arcuate arm (but not so far as to create a continuous ring), while in other embodiments, the track may not extend beyond either or both ends of the arcuate arm. The track is fixed in position relative to the arcuate arm.

The source drive mechanism 132 may be or comprise a motor or any other force-producing device or system. The source drive mechanism 132 may engage the arcuate arm or a track mounted thereto directly, or may comprise one or more gears, wheels, or other devices suitable for force-transmitting communication useful for causing the source 112 to move relative to the arcuate arm.

Operation of the source drive mechanism 132 may be controlled by the processor 104 and/or by a controller separate from the processor 104. The source drive mechanism 132 may be selectively activated to move the source 112 into a desired position prior to or following imaging of a patient or object, and/or may be selectively activated to cause the source 112 to move relative to the arcuate arm during imaging of a patient or object. Any motor or other torque-producing device or system, whether electric or otherwise, may be used for the source drive mechanism 132.

The detector drive mechanism 136 is configured to cause the detector 116 to move along an inner arc or circumferential surface of an arcuate arm of the imaging device 102 (and thus to move around an axis of the arcuate arm while remaining equidistant from that axis). The detector drive mechanism 136 may be configured to engage a track that is built into, extends from, is secured to, or is otherwise arranged along or proximate an inner arc or circumferential surface of the arcuate arm. In some embodiments, the detector drive mechanism 136 may be configured to engage a track that is the same as or similar to the track described above with respect to the source drive mechanism 132, or any other track described herein.

The detector drive mechanism 136 may be or comprise a motor or any other force-producing device or system. The detector drive mechanism 136 may engage the arcuate arm or a track associated therewith directly, or may comprise one or more gears, wheels, or other devices suitable for force-transmitting communication useful for causing the detector 116 to move relative to the arcuate arm.

Operation of the detector drive mechanism 136 may be controlled by the processor 104 and/or by a controller separate from the processor 104. In some embodiments, the detector drive mechanism 136 may be controlled by a controller other than the processor 104 that also controls the source drive mechanism 132. The detector drive mechanism 136 may be selectively activated to move the detector 116 into a desired position prior to or following imaging of a patient or object, and/or may be selectively activated to cause the detector 116 to move relative to the arcuate arm during imaging of a patient or object. Any motor or other torque-producing device or system, whether electric or otherwise, may be used for the detector drive mechanism 136.

The source drive mechanism 132 and the detector drive mechanism 136 may be controlled by a processor 104 or one or more controllers to ensure that the source 112 and the detector 116 remain approximately 180° apart (as measured from a center of the source 112 and a center of the detector 116) relative to the axis of the arcuate arm, so as to enable radiation emitted from the source 112 to be received by the detector 116. Where a type of radiation emitted by the source 112 is best detected from a position other than opposite from the source 112, the detector 116 may be separated from the source 116 by an angle other than 180°.

In some embodiments of the imaging device 102, the source 112 and the detector 116 may be independently movable relative to each other, such that operation of the source drive mechanism 132 and the detector drive mechanism 136 is solely responsible for maintaining a needed or preferred relative position of the source 112 to the detector 116 (or vice versa). Some embodiments of the imaging device 102 may be, use, or comprise one or more concepts or features described in one or more of U.S. Pat. No. 10,159,453, issued Dec. 25, 2018 and entitled "Transformable Imaging System"; U.S. Pat. No. 9,962,133, issued May 8, 2018 and entitled "Transformable Imaging System"; and/or U.S. Pat. No. 9,855,015, issued Jan. 2, 2018 and entitled "Transformable Imaging System," the entirety of each of which is hereby incorporated herein by reference. For example, embodiments of the imaging device 102 may utilize one or more aspects of one or more of the foregoing references regarding the independent control and movement of a source and/or a detector.

In other embodiments of the imaging device 102, the source 112 and the detector 116 may be mechanically fixed to each other in a needed or preferred relative position, such that movement of the source 112 results in a corresponding movement of the detector 116 and vice versa. In such embodiments, only one of the source drive mechanism 132 and the detector drive mechanism 136 may be needed to control the position of the source 112 and the detector 116.

The database 140 may store one or more images taken by one or more imaging devices 102 and may be configured to provide one or more such images (electronically, in the form of image data) to the imaging device 102 (e.g., for display on or via a user interface 120) or to any other device, whether directly or via the cloud 144. In some embodiments, the database 140 may be or comprise part of a hospital image storage system, such as a picture archiving and communication system (PACS), a health information system (HIS), and/or another system for collecting, storing, managing, and/or transmitting electronic medical records including image data.

The cloud 144 may be or represent the Internet or any other wide area network. The imaging device 102 may be connected to the cloud 144 via the communication interface 108, using a wired connection, a wireless connection, or both. In some embodiments, the imaging device 102 may communicate with the database 140 and/or an external device (e.g., a computing device) via the cloud 144.

Figure 1B:
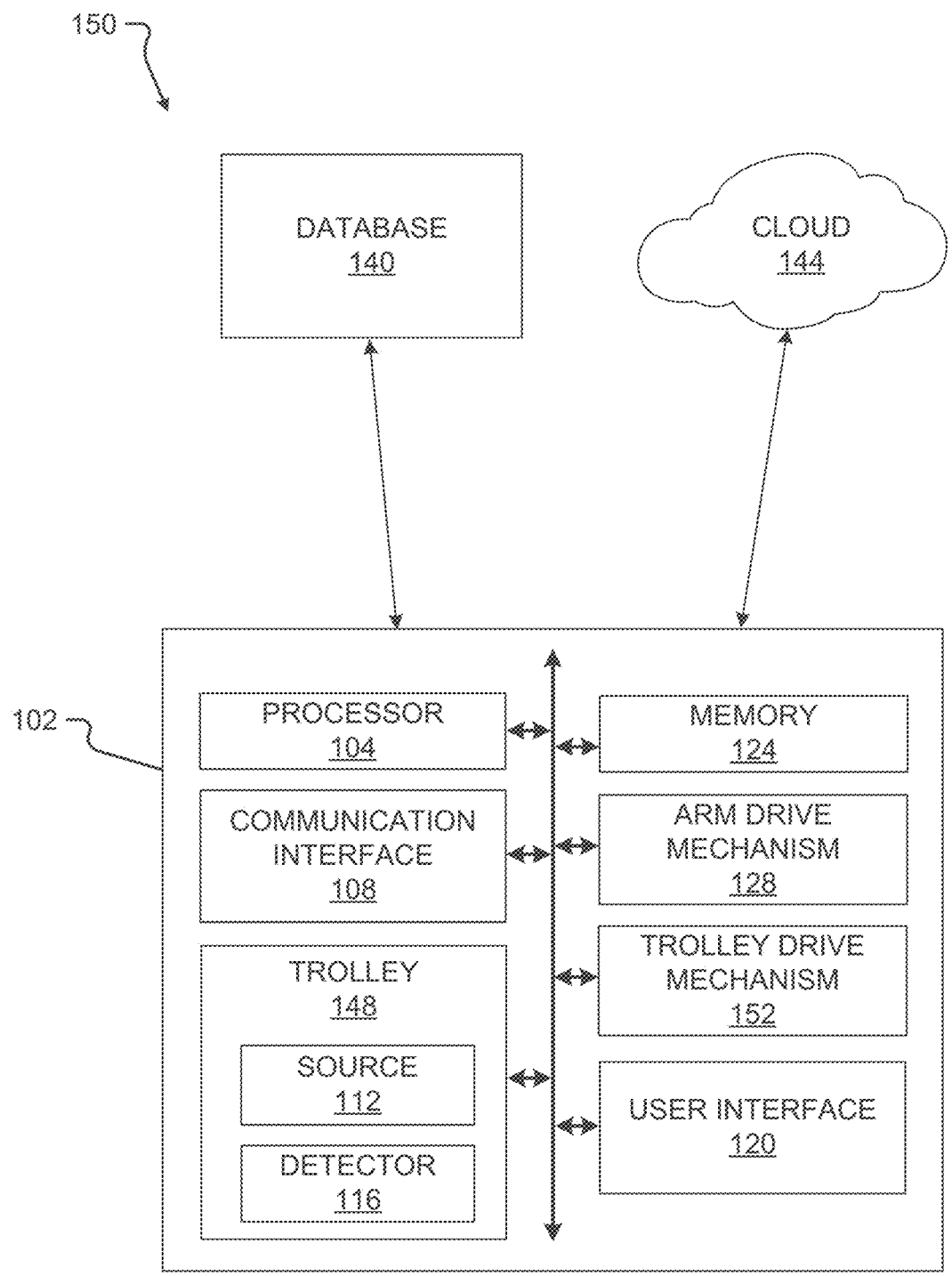
FIG. 1B is a block diagram of another system according to at least one embodiment of the present disclosure.

Turning now to FIG. 1B, a system 150 comprises an imaging device 102, a database 140, and a cloud 144. Each component of the system 150 is the same as or substantially similar to the corresponding component in the system 100, except that the imaging device 102 comprises a trolley 148 to which the source 112 and detector 116 are fixedly secured, and the source drive mechanism 132 and the detector drive mechanism 136 are replaced by a trolley drive mechanism 132. The trolley 148 may have, for example, an arcuate shape with a curvature that matches a curvature of an arcuate arm of the imaging device 102.

The trolley 148 may be any structure movably attached to an arcuate arm of the imaging device 102 and configured to support the source 112 and the detector 116. In embodiments of the imaging device 102 comprising one or more tracks built into, extending from, secured to, or otherwise arranged along or proximate a surface of the arcuate arm, the trolley may be configured to selectively roll or otherwise move along the one or more tracks, so as to change the position of the source 112 and the detector 116 relative to the arcuate arm. In some embodiments, a plurality of trolleys 148 may be used, each configured to movably secure one of the source 112 and the detector 116 to the arcuate arm or to one or more tracks of the imaging device 102.

The source 112 and the detector 116 may be separated from each other on the trolley 148 by approximately 180° (as measured from a center of the source 112 and a center of the detector 116), or by less than 180°.

The trolley drive mechanism 152 is configured to cause the trolley 148 to move along an inner arc or circumferential surface of an arcuate arm of the imaging device 102 (and thus to move around an axis of the arcuate arm while remaining equidistant from that axis). The trolley drive mechanism 152 may be configured to engage a track that is built into, extends from, is secured to, or is otherwise arranged along or proximate an inner arc or circumferential surface of the arcuate arm. In some embodiments, the trolley drive mechanism 152 may be configured to engage a track that is built into, extends from, is secured to, or is otherwise arranged along or proximate one or both axial side surfaces or ends of the arcuate arm. Any such track may extend along an entirety of the arcuate arm or along a portion of the arcuate arm.

The trolley drive mechanism 152 may be or comprise a motor or any other force-producing device or system. The trolley drive mechanism 152 may engage the arcuate arm or a track mounted thereto directly, or may comprise one or more gears, wheels, or other devices suitable for force-transmitting communication useful for causing the trolley 148 to move relative to the arcuate arm. In embodiments of the imaging device 102 that comprise more than one trolley 148, the imaging device 102 may comprise a separate trolley drive mechanism 152 for each trolley 148, or a single trolley drive mechanism 152 in force-transmitting communication with each trolley 148.

Operation of the trolley drive mechanism 152 may be controlled by the processor 104 and/or by a controller separate from the processor 104. The trolley drive mechanism 148 may be selectively activated to move the trolley 148 into a desired position prior to or following imaging of a patient or object, and/or may be selectively activated to cause the trolley 148 to move relative to the arcuate arm during imaging of a patient or object. Any motor or other torque-producing device or system, whether electric or otherwise, may be used for the trolley drive mechanism 148.

Figure 2:
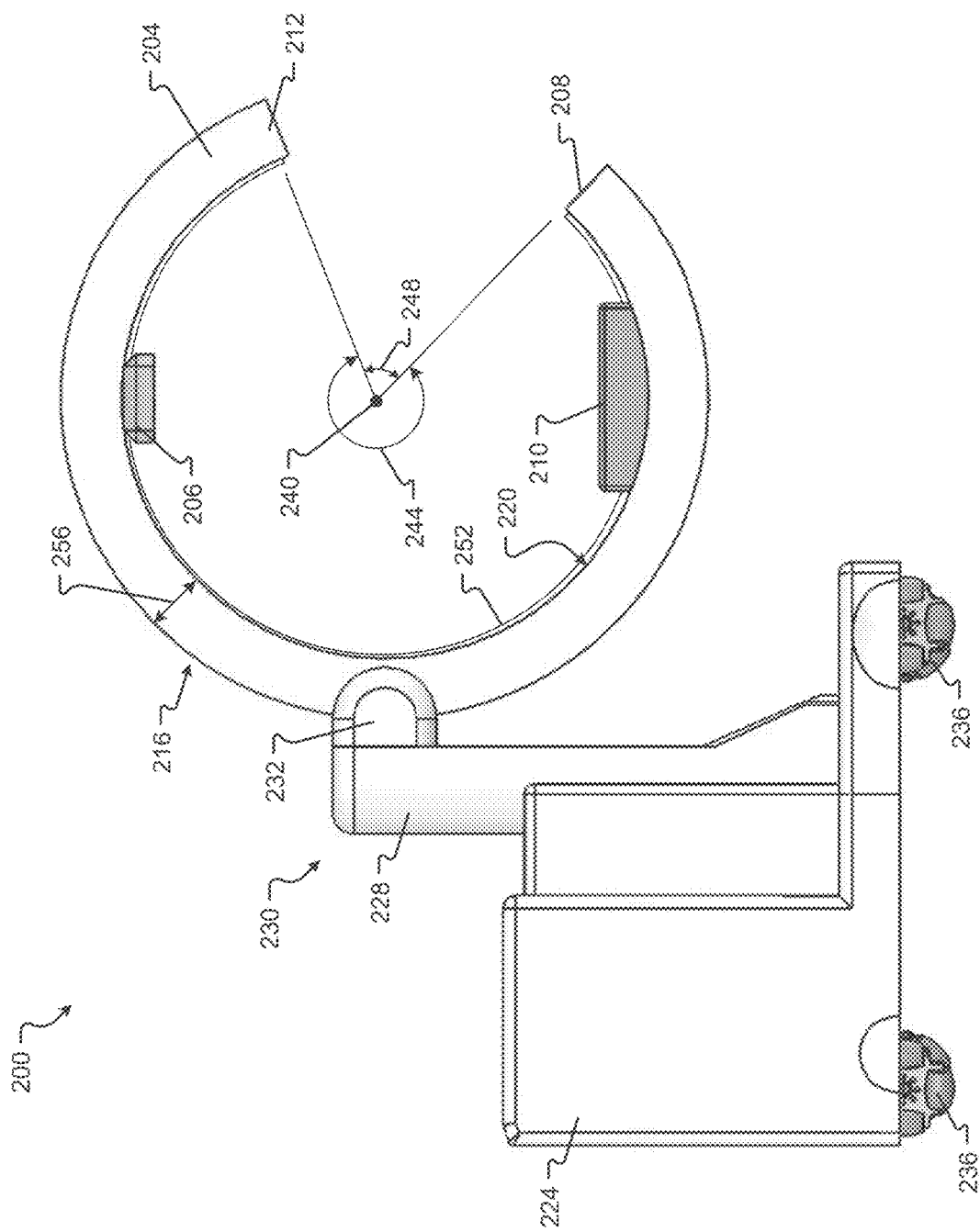
FIG. 2 is an elevation view of a G-shaped arm imaging device according to at least one embodiment of the present disclosure.

With respect to FIG. 2, an imaging device 200 may be the same as or similar to the imaging device 102 of the systems 100 and/or 150, described above. The imaging device 200 comprises an arcuate arm 204, a support structure 230, and a base 224.

The arcuate arm 204 is an open ring. In other words, the arcuate arm does not define a full circle, but rather extends around an axis 240 from a first end 208 to a second end 212. The first end 208 and the second end 212 are fixed relative to each other. Thus, regardless of the rotation of the arcuate arm 204 about the axis 240, the first end 208 and the second end 212 remain separated by the same distance (whether angular, linear, or otherwise). The arcuate arm 204 comprises an outer surface 216 that defines an outer arc around the axis 240 and extends from the first end 208 to the second 212. The arcuate arm 204 also comprises an inner surface 220 that defines an inner arc around the axis 240 and extends from the first end 208 to the second end 212. The outer surface 216 is separated from the inner surface 220 by a radial distance 256. Each of the outer arc (defined by the outer surface 216) and the inner arc (defined by the inner surface 220) extends through an angle or arc measure 244 relative to the axis 240. The angle or arc measure 244 may be anywhere between approximately 180° and 350°. The first end 208 and the second end 212 are separated from each other by an angle 248 (again relative to the axis 240) that is equal to 360° minus the angle or arc measure 244. For example, if the angle 244 is 300°, then the angle 248 is equal to 360° minus 300°, which equals 60°. As another example, if the arc measure 244 is 180°, then the angle 248 is equal to 360° minus 180°, which is also equal to 180°.

The arcuate arm 204 may in some embodiments comprise one or more tracks 252 to which a source assembly 206 and/or a detector assembly 210 may be mounted. The source assembly 206 may comprise or house, for example, a source 112 and a source drive mechanism 132. The detector assembly 210 may comprise or house, for example, a detector 116 and a detector drive mechanism 136. In some embodiments, some or all of the source drive mechanism 132 and the detector drive mechanism 136 may be positioned inside the arcuate arm 204.

The track 252 is connected to or otherwise extends adjacent to the inner surface 220. In other embodiments, however, the track 252 may be connected to or otherwise extend adjacent to an axial side surface of the arcuate arm 204 (extending, for example, between the outer surface 216 and the inner surface 220). Also in some embodiments, the track 252 may be defined by the inner surface 220 of the arcuate arm 204, or may be secured in between the inner surface 220 and the outer surface 216 (in which embodiments the track 252 may be accessible, for example, via a slot in the inner surface 220 or in a side surface of the arcuate arm 204 that extends between the outer surface 216 and the inner surface 220). The track 252 may be or comprise one or more rails, flanges, rollers, conveyors, magnets, electromagnets, or other devices or systems configured to movably support the source 112 and/or the detector 116. The track 252 is fixed relative to the arcuate arm 204. In some embodiments, the track 252 does not extend beyond the first end 208 or the second end 212, while in other embodiments, the track 252 may extend beyond the first end 208 and/or the second end 212, but still does not form a closed ring.

In some embodiments, the arcuate arm 204 may comprise 2 or more parallel tracks 252 extending from proximate the first end 208 to proximate the second end 212. In other embodiments, the arcuate arm 204 may comprise separate tracks 252 for each of the source assembly 206 and the detector assembly 210. In such embodiments, the separate tracks 252 may each extend along the arcuate arm 204 through an angle that is equal to or greater than the angle 248.

In embodiments of the present disclosure that utilize a trolley 148, the trolley 148 may have an arcuate shape with a curvature that is the same as or similar to the curvature of the arcuate arm 204. The trolley 148 may extend from a third end proximate the first end 208 to a fourth end proximate the second end 212. The third end of the trolley 148 may be separated from a fourth end of the trolley 148 by an angular distance of approximately 180°. The trolley 148 may be directly connected to or otherwise configured to engage with the track 252, while the source 112 and the detector 116 are secured to the trolley 148 in between the third end and the fourth end of the trolley 148. In such embodiments, the track 252 may be one or more continuous or substantially continuous tracks that extend from the first end 208 to the second end 212, or the track 252 may comprise a plurality of tracks 252 that are separated from each other by an angular distance around the axis 240, and the trolley 148 may be configured to engage each of the tracks 252 separately so as to be able to rotate around the axis 240. In some embodiments, the third end of the trolley 148 may never pass the first end 208 of the arcuate arm 204, and the fourth end of the trolley 148 may never pass the second end 212 of the arcuate arm 204. In other embodiments, the third end of the trolley 148 may pass the first end 208 and/or the second end 212 of the arcuate arm 204, but not by so much that the trolley 148 bridges the gap between the first end 208 and the second end 212.

The arcuate arm 204 is rotatably supported by a support structure 230. In some embodiments, the support structure 230 may comprise a tower 228 and an extension or support arm 232. The support structure 230 may also support an arm drive mechanism 128 for causing the arcuate arm 204 to rotate about its axis 240. The support arm 232 may be configured to grip one or two flanges extending axially (e.g., parallel to the axis 240) from one or both sides of the outer surface 216. The support arm 232 may be configured to grip the side surfaces of the arcuate arm 204 (e.g., surfaces extending in between the outer surface 216 and the inner surface 220). In some embodiments, the support arm 232 may comprise one or more projections configured to extend into one or more slots on one or more surfaces of the arcuate arm 204, so as to grip the arcuate arm 204 either entirely or partially from inside the arcuate arm 204.

The support arm or extension 232 may further house some or all of an arm drive mechanism 128 configured to selectively rotate the arcuate arm 204 about the axis 240. The arcuate arm 204 may be selectively rotatable about the axis 240 through an angle of rotation substantially equal to the angle 244. For example, an arm drive mechanism 128 within the extension 232 may be configured to rotate the arcuate arm 204 from proximate the first end 208 to proximate the second end 212.

The tower 228 is sized to ensure that the arcuate arm 204 is positioned at a height that enables the imaging device 200 to be positioned to take a 360° scan of a patient on an operating table or other platform. With the open space between the first end 208 and the second end 212 positioned as shown in FIG. 2 (e.g., opposite the support arm 232), the imaging device 200 can be maneuvered toward the side of the operating table or other platform until a length of the operating table is substantially aligned (with or without an offset) with the axis 240. In this position, the arcuate arm 204 can be rotated around the axis 240 by the arm drive mechanism 128 within the extension 232 without contacting the operating table or a patient positioned on the operating table.

In some embodiments, the tower 228 may be adjustable to adjust a height of the extension 232 and thus of the arcuate arm 204. In such embodiments, the tower 228 may be manually adjustable or automatically adjustable.

The tower 228 is supported by a base 224, which rests on a plurality of wheels 236. The base 224 may also house or support, for example, a processor 104, a communication interface 108, a user interface 120, a memory 124, a power source, and/or any other component of the imaging device 200.

The wheels 236 may be omni-directional wheels. One or more of the wheels 236 may be a caster wheel. One or more of the wheels 236 may be the same as or similar to the omni-directional wheels described in U.S. Patent Application Publication No. 2019/0099140 (application Ser. No. 16/144,058) and/or U.S. Patent Application Publication No. 2019/0099141 (application Ser. No. 16/144,103), both filed Sep. 27, 2018 on behalf of applicant Medtronic Navigation, Inc. (referred to hereinafter as the "'140 Publication" and "'141 Publication, respectively), the entirety of each of which is hereby incorporated herein by reference. The wheels 236 may be mounted to the base via any structure described in the '140 Publication and/or the '141 Publication, or via any other structure suitable for enabling the wheels 236 to support the base 224.

Additionally, one or more of the wheels 236 may be driven and/or undriven. Where one or more of the wheels 236 is driven, the drive mechanism in force-transmitting communication with the one or more wheels 236 may be the same as or similar to any drive mechanism described in the '140 Publication and/or the '141 Publication. The drive mechanism may comprise one motor configured to drive one or a plurality of the wheels 236, or a plurality of motors, each configured to drive one or more of the wheels 236. In some embodiments, each driven wheel 236 may be in force-transmitting communication with a separate motor. The drive mechanism may be controlled by one or more user interfaces such as the user interface 120, which may be provided on or near the base 224 and/or may be separate from but in remote communication with the base 224 via the communication interface 108.

The wheels 236 may be configured to allow the imaging device 200 to move or be moved forward, backward, sideways, or in any other direction. One or more of the wheels 236 may be selectively lockable. For example, one or more of the wheels 236 may be placed in an unlocked configuration to allow for movement and positioning of the imaging device 200, and in a locked configuration to prevent movement of the imaging device 200 during operation or storage thereof.

Figure 3B:
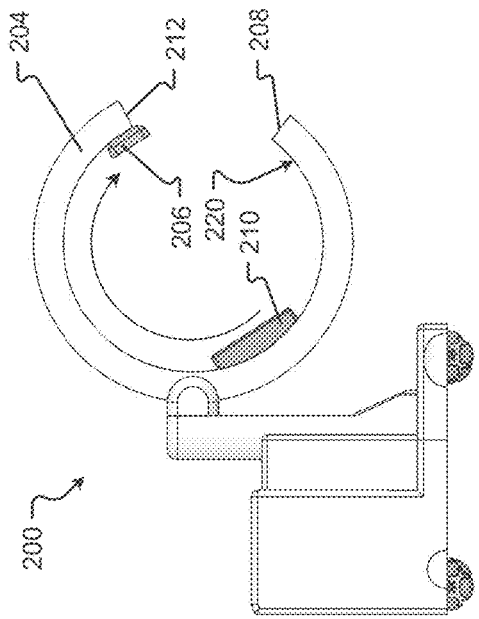
FIG. 3B is an elevation view of a G-shaped arm imaging device according to at least one embodiment of the present disclosure in a second configuration.
Figure 3D:
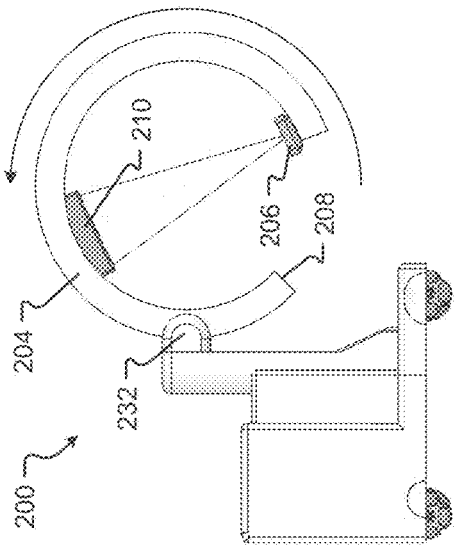
FIG. 3D is an elevation view of a G-shaped arm imaging device according to at least one embodiment of the present disclosure in a fourth configuration.
Figure 3A:
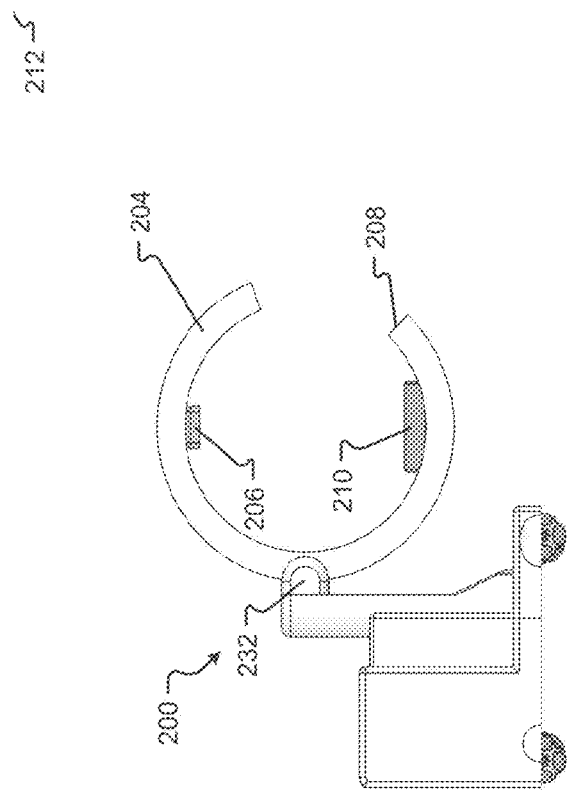
FIG. 3A is an elevation view of a G-shaped arm imaging device according to at least one embodiment of the present disclosure in a first configuration.

FIGS. 3A-3G illustrate how the imaging device 200 may accomplish a 360° scan despite the arcuate arm 204 not forming a complete circle. With the arcuate arm 204 positioned such that the opening in the arm 204 is opposite the support arm 232, as shown in FIG. 3A, the imaging device 200 may be moved into position relative to a patient or other object to be imaged. For example, if a patient is positioned on an operating table, the imaging device 200 may be moved such that the arcuate arm 204 partially surrounds the patient and operating table (e.g., with a length of the patient/operating table aligned with the axis 240 of the arcuate arm 204).

To set up for the 360° scan, the source assembly 206 and the detector assembly 210 may each rotate or be caused to rotate clockwise (whether on the track 252 or otherwise) around or proximate the inner surface 220, as shown in FIG. 3B. The movement may continue until the source assembly 206 or the detector assembly 210 is proximate the second end 212. In other embodiments, the source assembly 206 and the detector assembly 210 may each rotate counter-clockwise (whether on the track 252 or otherwise) around or proximate the inner surface 220, until the detector assembly 210 or the source assembly 206 is proximate the first end 208.

Depending on how the source assembly 206 and detector assembly 210 are secured to or otherwise engage with the track 252 or otherwise to the arm 204, each may be capable of extending slightly past the second end 212 or the first end 208, respectively. However, a midpoint of the source assembly 206 never passes beyond the second end 212, and a midpoint of the detector assembly never passes beyond the first end 208 (or vice versa). Neither the source assembly 206 nor the detector assembly 212 ever bridges the gap between the first end 208 and the second end 212. In other words, to get from the first end 208 to the second end 212 or vice versa, both the source assembly 206 and the detector assembly 210 must travel along the arcuate arm 204.

Where proper operation of the source 112 and the detector 116 requires that the two devices remain approximately 180° apart, the source assembly 206 and the detector assembly 210 may remain approximately 180° apart during this movement, or the separation between the two devices may vary during the movement but end up at approximately 180° of separation when the movement is complete.

Figure 3C:
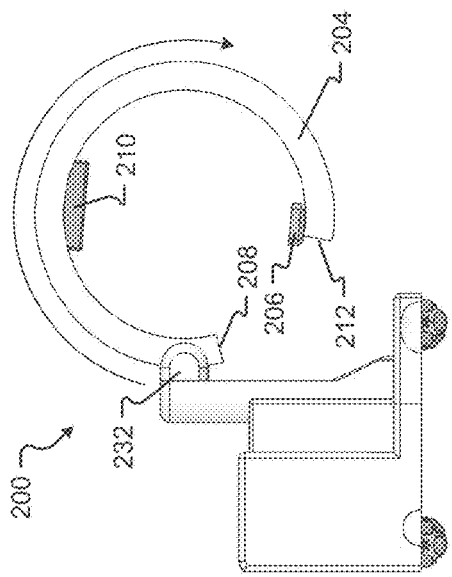
FIG. 3C is an elevation view of a G-shaped arm imaging device according to at least one embodiment of the present disclosure in a third configuration.

Either simultaneously with or after the movement of the source assembly 206 and the detector assembly 210 described above, the arcuate arm 204 is rotated around the axis 240 in a clockwise direction until the first end 208 is proximate the support arm 232, as shown in FIG. 3C. In some embodiments, the arcuate arm 204 may be rotated around the axis 240 in a counterclockwise direction until the second end 212 is proximate the support arm 232.

Figure 3F:
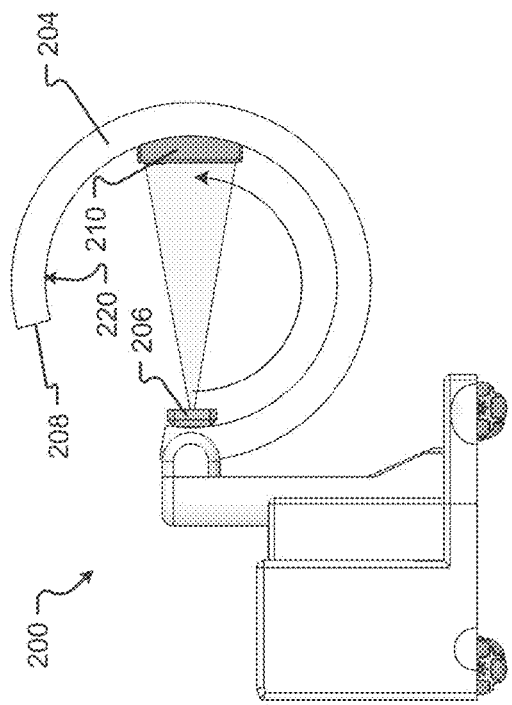
FIG. 3F is an elevation view of a G-shaped arm imaging device according to at least one embodiment of the present disclosure in a sixth configuration.
Figure 3E:
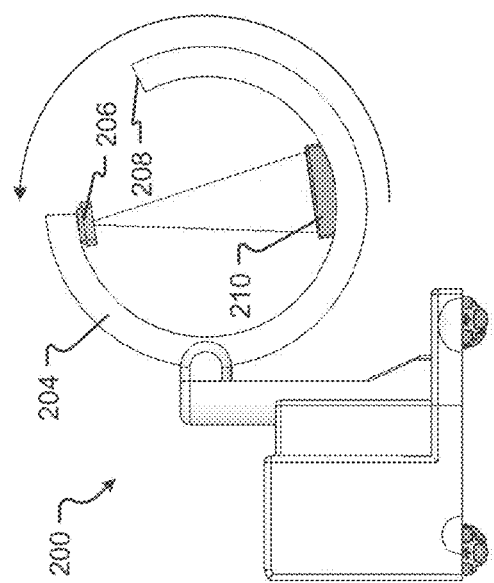
FIG. 3E is an elevation view of a G-shaped arm imaging device according to at least one embodiment of the present disclosure in a fifth configuration.

With the source assembly 206 proximate the second end 212, and the arcuate arm 204 rotated until the first end 208 is proximate the support arm 232 (or, in other embodiments, with the detector assembly 210 proximate the first end 208, and the arcuate arm 204 rotated until the second end 212 is proximate the extension 232), the imaging device 200 may commence imaging or scanning by activating the source 112 (of the source assembly 206) and the detector 116 (of the detector assembly 210), as illustrated in FIGS. 3D and 3E. With the source 112 and the detector 116 operational, the arcuate arm 204 is rotated in a counterclockwise direction, while the source assembly 206 and the detector assembly 210 remain fixed in position relative to the arcuate arm 204. In this way, movement of the arcuate arm 204 causes the source assembly 206 and the detector assembly 210 to rotate about the axis 204 by an angle X that is approximately equal to the angle or arc measure 244. For example, if the arcuate arm extends through an angle or arc measure 244 of 300° around the axis 240, then rotation of the arcuate arm 204 from the first end 208 to the second end 212 will result in rotation of the source assembly 206 and the detector assembly 210 about the axis 240 through an angle X of approximately 300°. Where the extension 232 is not able to rotate or grip the arcuate arm 204 all the way to the first end 208 and/or the second end 212, the angle of rotation X will be somewhat less than the angle or arc measure 244. In no event, of course, will the angle of rotation X be greater than the angle 244, because the support arm 232 would be able to grip the arcuate arm 204 beyond the first end 208 or the second end 212, which are separated by the angle or arc measure 248.

When the arcuate arm 204 has rotated from proximate the first end 208 to proximate the second end 212, the source assembly 206 and detector assembly 210 will have rotated about the axis 240 by an angle X of at least 180° and by no more than the angle 244. As the arcuate arm 204 reaches the limit of rotation (as defined by the second end 212 in the embodiment illustrated in FIG. 3F, or by the first end 208 in other embodiments), the source assembly 206 and detector assembly 210 begin to rotate along or proximate to the inner surface 220 in a counterclockwise direction, as shown in FIG. 3F. Alternatively, in embodiments where the arcuate arm 204 was rotating in a clockwise direction, the source assembly 206 and the detector assembly 210 begin to rotate along or proximate to the inner surface 220 in a clockwise direction. The source assembly 206 and the detector assembly 210 continue to rotate through an angle Y about the axis 240, which angle Y is greater than or equal to the angle 248, and/or is greater than or equal to 360° minus the angle X. So, for example, if the arcuate arm 204 defines an angle or arc measure 244 of 300°, and the extension 232 is able to rotate the arcuate arm 204 (and thus the source assembly 206 and the detector assembly 210) through an angle X of 280°, then the source assembly 206 and the detector assembly 210 will continue to rotate along or proximate the inner surface 220 around the axis 240 by an angle Y that is equal to or greater than 360° minus 280°, or 80°. As another example, if the arcuate arm 204 defines an angle or arc measure 244 of 200°, and the extension 232 is able to rotate the arcuate arm 204 (and thus the source assembly 206 and the detector assembly 210) through an angle X of 180°, then the source assembly 206 and the detector assembly 210 will continue to rotate along or proximate the inner surface 220 around the axis 240 by an angle Y that is equal to or greater than 360° minus 180°, which equals 180°.

Figure 3G:
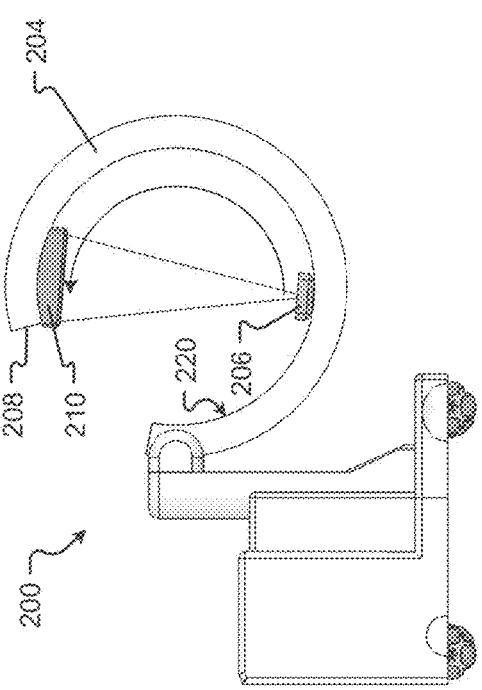
FIG. 3G is an elevation view of a G-shaped arm imaging device according to at least one embodiment of the present disclosure in a seventh configuration.

As shown in FIG. 3G, the source assembly 206 and the detector assembly 210 may rotate through the angle Y until the detector assembly 210 reaches or is proximate to the first end 208. At this point, the source assembly 206 and the detector assembly 210 will have completed a full 360° scan of the patient or other object positioned along the axis 240, without need for an O-arm or other complete ring about the patient or other object.

As may be appreciated, in embodiments where both a source 112 and a detector 116 are not needed, such as for imaging devices 200 that utilize an optical sensor, only the optical sensor may be caused to rotate around the axis 240. In such embodiments, however, the same principle of operation applies: a full 360° of rotation may be accomplished by moving the arcuate arm 204 through a first angle of rotation, and by moving the imaging sensor through a second angle of rotation less than or equal to the first angle of rotation, provided that the sum of the first and second angles of rotation is 360°.

In some embodiments, the imaging device 200 may accomplish a complete 360° scan by first causing the imaging sensor(s) (e.g., the source 112 and the detector 116) to rotate along or proximate to the inner surface 220 of the arcuate arm 204, and then by causing the arcuate arm 204 to rotate while the imaging sensor(s) remain fixed in position relative to the arcuate arm 204. In such embodiments, as in other embodiments described above, the angle Y of rotation of the imaging sensor(s) about the axis 240 relative to the arcuate arm 204 will be less than the angle X of rotation of the arcuate arm 204 about the axis 240, and the sum of the angles X and Y will be at least 360°.

Figure 4:
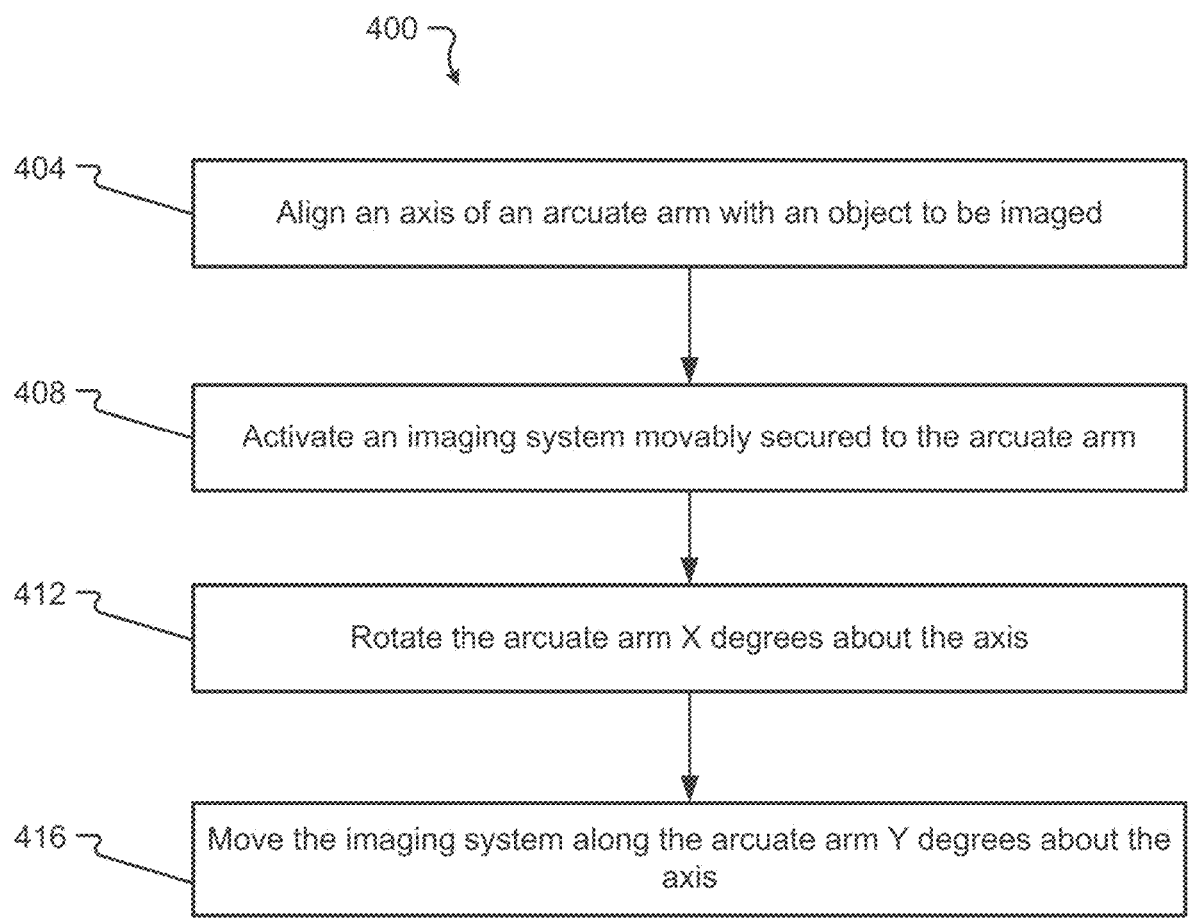
FIG. 4 is a flowchart of a method according to at least one embodiment of the present disclosure.

Turning now to FIG. 4, a method 400 according to at least some embodiments of the present disclosure comprises aligning an axis of an arcuate arm of an imaging device with an object to be imaged (step 404). The arcuate arm may be the same as or similar to, for example, the arcuate arm 204 described with respect to FIGS. 2-3G. The arcuate arm may define a central axis and may extend along an arc about that central axis through an arc measure between 180° and 345° or 350°, or an arc measure between 210° and 320°, or an arc measure between 270° and 300°.

Aligning an axis of the arcuate arm with an object to be imaged may comprise moving—forward, backward, sideways, around an axis, and/or in any other direction or motion—an imaging device that comprises the arcuate arm, such as the imaging device 102 or 200. The alignment may occur automatically. For example, in some embodiments, the arcuate arm may be held by an arm that is supported by a fixed base (e.g., a wall, a floor, a ceiling, or otherwise), and configured for imaging a patient positioned on a table that has a fixed position relative to the arcuate arm (or that can be moved to a known position relative to the arcuate arm). In such embodiments, the arcuate arm may be positioned in a retracted position (where no part of the table extends through a circle that includes an arc of the arcuate arm) initially (for example, so that a patient can be positioned on the table). The arcuate arm may then be moved such that an axis of the arcuate arm is aligned with a length of the table or patient, from which position the arcuate arm may be rotated about its axis without impacting the table or the patient. Once the imaging is complete, the arcuate arm may be moved again to a retracted position, to facilitate the patient's removal or exit from the table. In other embodiments, automatic alignment may utilize one or more sensors on the imaging device, the operating table, and/or one or more external devices or systems (e.g., a navigation system) to automatically cause the imaging device to move so as to align the arcuate arm with a patient or an object to be imaged.

In other embodiments, aligning an axis of the arcuate arm with an object to be imaged may comprise manually positioning an imaging device comprising the arcuate arm (e.g., by pushing and/or pulling the imaging device) so that the subject to be imaged (whether animate or inanimate) is aligned with the axis of the arcuate arm. In such embodiments, the imaging device and/or a component thereof may be supported by one or more omnidirectional wheels, which may facilitate movement of the imaging device in any direction necessary to align the axis of the arcuate arm with the object to be imaged.

Aligning an axis of the arcuate arm with an object to be imaged may comprise positioning the arcuate arm such that an open portion thereof (e.g., an empty space between a first end and a second end thereof) is positioned opposite an extension or other support structure that supports the arcuate arm.

The method 400 may also comprise activating an imaging system movably secured to the arcuate arm (step 408). The imaging system may comprise a source (such as the source 112) and a detector (such as the detector 116). The imaging system may comprise a single sensor (e.g., an optical sensor) or a plurality of sensors. The imaging system may obtain images by emitting and detecting X-rays, or by emitting and detecting another kind of radiation, or by detecting radiation that is emitted independently of the imaging device (e.g., light).

The imaging system may be movably secured to the arcuate arm via one or more drive mechanisms (e.g., a source drive mechanism 132 and a detector drive mechanism 136, or a trolley drive mechanism 152). The arcuate arm may comprise one or more tracks, such as the tracks 252, that are engaged by the one or more drive mechanisms or a portion thereof. In some embodiments, the source and detector and/or other imaging sensor(s) may be fixedly secured to a trolley, which in turn may be movably secured to the arcuate arm and configured to move along or proximate a surface thereof, whether via a track or otherwise.

The imaging system may be activated manually (e.g., in response to a user action such as flipping a switch or pressing a button), automatically (e.g., as a result of execution by a processor such as the processor 104 of one or more instructions stored in a memory 124), or by any combination thereof.

The method 400 may further comprise rotating the arcuate arm X degrees about the axis (step 412), where X has a minimum value of at least 180° and a maximum value defined by an angular distance along the arcuate arm between a first end and a second end of the arcuate arm. The rotating may be accomplished using an arm drive mechanism such as the arm drive mechanism 128, which may apply a torque, for example, directly to an outer surface of the arcuate arm (such as the outer surface 216), or directly to one or more side surfaces of the arcuate arm, or to one or more gear teeth or other protrusions extending from a surface of the arcuate arm, or to a track extending from or built into an outer surface and/or one or more side surfaces of the arcuate arm.

The method 400 may yet further comprise moving the imaging system along the arcuate arm Y degrees about the axis (step 416), where Y has a minimum value of at least 360° minus X, such that the sum of X and Y is at least 360°. Moving the imaging system along the arcuate arm may comprise, for example, activating a source drive mechanism 132 and/or a detector drive mechanism 136. Moving the imaging system along the arcuate arm may alternatively comprise, for example, activating a trolley drive mechanism 152. Moving the imaging system along the arcuate arm may comprise causing the imaging system or one or more components thereof to move along a track that is defined by, secured to, built into, or otherwise positioned along the arcuate arm.

As may be appreciated based on the foregoing disclosure, the present disclosure encompasses methods with fewer than all of the steps identified in FIG. 4 and the corresponding description, as well as methods that include more steps than those identified in FIG. 4 and the corresponding description. In some embodiments, one or more steps of the method 400 may be repeated one or more times.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An imaging device comprising:
   an open ring having a first end, a second end, and an axis, the open ring defining an outer arc and an inner arc;
   a support arm configured to support the open ring and to rotate the open ring about the axis;
   a track extending along the open ring;
   a source movably disposed on the track and operable to generate signals useful for imaging; and
   a detector movably disposed on the track, the detector operable to detect signals generated by the source;
   wherein movement of the source and detector along the track, coupled with rotation of the open ring about the axis, enables the source and detector to travel at least 360 degrees about the axis, and
   wherein movement of the source and the detector along the track is selectively independent of rotation of the open ring relative to the support arm.

2. The imaging device of claim 1, wherein the track does not extend beyond the first end or the second end.

3. The imaging device of claim 1, wherein the source and the detector are positioned 180 degrees apart around the track.

4. The imaging device of claim 3, further comprising;
   a trolley movably disposed on the track, the trolley extending between a third end proximate the first end and a fourth end proximate the second end,
   wherein the source and the detector are fixedly secured to the trolley between the third end and the fourth end, the third end never passes the first end, and the fourth end never passes the second end.

5. The imaging device of claim 1, wherein each of the source and the detector is movable along the track toward the first end and away from the first end.

6. The imaging device of claim 1, wherein the outer arc has an arc measure between 270 degrees and 350 degrees.

7. The imaging device of claim 1, further comprising:
   a base to which the support arm is secured, the base selectively movable on a plurality of omnidirectional wheels.

8. The imaging device of claim 1, wherein the track extends along the inner arc.

9. The imaging device of claim 1, wherein each of the source and the detector is configured to move along the track through an arc of 90 degrees or less.

10. The imaging device of claim 1, wherein a distance between the first end and the second end is fixed.

11. An imaging device comprising:
an open ring having a first end, a second end, and an axis, the open ring defining an outer arc and an inner arc;
a support arm configured to support the open ring and to rotate the open ring about the axis;
a track extending along the open ring;
a source movably disposed on the track and operable to generate signals useful for imaging; and
a detector movably disposed on the track, the detector operable to detect signals generated by the source;
wherein movement of the source and detector along the track, coupled with rotation of the open ring about the axis, enables the source and detector to travel at least 360 degrees about the axis, and
wherein each of the source and the detector is movable along the track toward the first end and away from the first end.

12. The imaging device of claim 11, wherein the track does not extend beyond the first end or the second end.

13. The imaging device of claim 11, wherein the source and the detector are positioned 180 degrees apart around the track.

14. The imaging device of claim 13, further comprising:
a trolley movably disposed on the track, the trolley extending between a third end proximate the first end and a fourth end proximate the second end,
wherein the source and the detector are fixedly secured to the trolley between the third end and the fourth end, the third end never passes the first end, and the fourth end never passes the second end.

15. The imaging device of claim 11, wherein movement of the source and the detector along the track is selectively independent of rotation of the open ring relative to the support arm.

16. The imaging device of claim 11, wherein the outer arc has an arc measure between 270 degrees and 350 degrees.

17. The imaging device of claim 11, further comprising:
a base to which the support arm is secured, the base selectively movable on a plurality of omnidirectional wheels.

18. The imaging device of claim 11, wherein the track extends along the inner arc.

19. The imaging device of claim 11, wherein each of the source and the detector is configured to move along the track through an arc of 90 degrees or less.

20. The imaging device of claim 11, wherein a distance between the first end and the second end is fixed.

* * * * *